United States Patent [19]

Baker

[11] 3,968,351
[45] July 6, 1976

[54] OBJECT CLASSIFICATION AND COUNTING MACHINE HAVING CORRECTION APPARATUS FOR REMOVING BIAS FROM COUNT

[75] Inventor: James D. Baker, Burnsville, Minn.

[73] Assignee: Honeywell Inc., Minneapolis, Minn.

[22] Filed: Sept. 13, 1973

[21] Appl. No.: 397,047

[52] U.S. Cl. .................. 235/92 PC; 235/92 PL; 235/92 ME; 235/92 R; 340/146.3 MA; 340/146.3 Y
[51] Int. Cl.² .................................. H03K 21/10
[58] Field of Search ...... 235/92 PC, 92 ME, 92 MS, 235/92 CP, 92 CT, 92 PL, 151.3, 151.35, 153 AP; 340/146.3 AC, 146.3 AQ, 146.3 MA, 146.3 S, 146.3 Y, 172.5

[56] References Cited
UNITED STATES PATENTS

| | | |
|---|---|---|
| 3,106,699 | 10/1963 | Kamentsky ............... 340/172.5 |
| 3,315,229 | 4/1967 | Smithline ................. 235/92 MS |
| 3,686,486 | 8/1972 | Coulter et al. ............ 235/92 PC |
| 3,836,850 | 9/1974 | Coulter .................... 235/92 PC |
| 3,873,974 | 3/1975 | Bouton et al. ............ 340/146.3 AC |

Primary Examiner—Gareth D. Shaw
Assistant Examiner—John P. Vandenburg
Attorney, Agent, or Firm—Omund R. Dahle

[57] ABSTRACT

A machine which classifies objects on the basis of an analysis of certain features related to that object, an example of which is a blood cell analyzer/counter, is subject to a number of random errors in recognition, which errors on the average tend to appear as a systematic bias. A correction device corrects for these errors to provide a more accurate count.

4 Claims, 2 Drawing Figures

OBJECT CLASSIFICATION AND COUNTING MACHINE HAVING CORRECTION APPARATUS FOR REMOVING BIAS FROM COUNT

BACKGROUND AND SUMMARY OF THE INVENTION

The type of machine of interest here is one that classifies objects by type and provides an estimate or count of the number of each type. If the machine is imperfect in terms of classification, then there will be a bias or error in the estimated number of objects in each category. If the machine is statistical in nature, in that the estimated number is a random variable, then there are also uncertainties due to this factor. It is possible, however, to make a standard correction such that the average error of the estimate is zero. An example is discussed for which this correction leads to a significant improvement in accuracy.

In the field of blood cell analyzer counters it is necessary to classify blood cells into about a half dozen categories or types and to count the number of cells of each category. A statistical bias occurs if there is any uncertainty in the classification process. These machines which classify objects on the bias of an analysis of certain features of that object are subject to misrecognizing a certain number of the objects. One reason for error comes from the practical problem of being able to consider only a limited number of features in the process of distinguishing objects. In this process of classifying and counting each category, the errors in classification are found to produce a bias which appears as a biased statistical error. It can be determined visually what the actual count of a sample is and compare it with the machine count to determine the bias or error of the machine. In the case of blood cell samples the actual count of cells of each blood cell type can be made manually by persons skilled at blood cell type recognition examining the slide sample under a microscope. The present invention corrects for recognition errors of a blood cell analyzer counter or of other batch processes in which various types of specimens are recognized and counted.

DESCRIPTION

Figure 1:
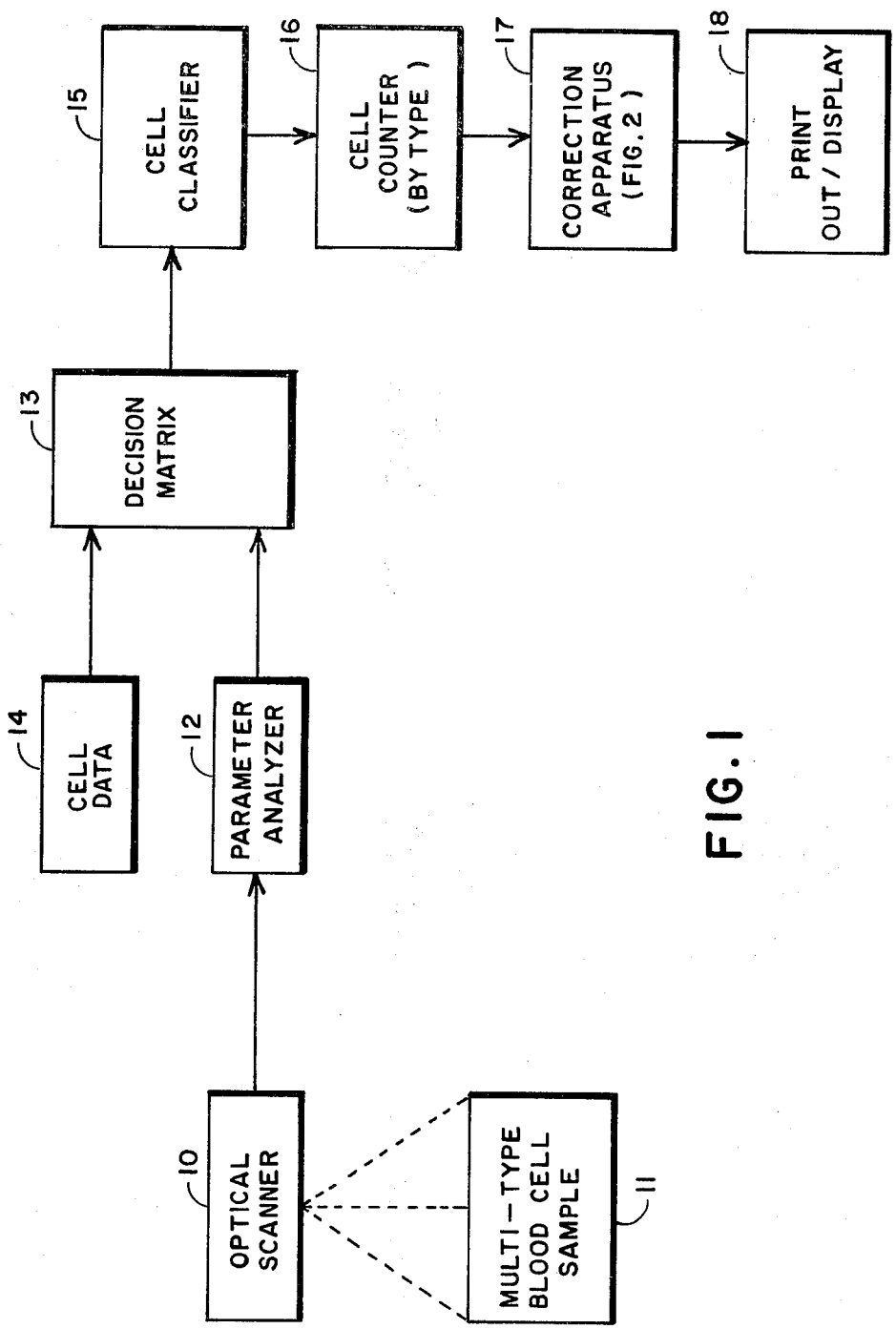
FIG. 1 is a block diagram of an object classification and counting system including the count correction of this invention; and, FIG. 2 is a more detailed schematic diagram of the count correction apparatus of FIG. 1.

In FIG. 1 a system is shown in which there is an optical scanner 10 positioned for viewing a sample 11 which sample comprises a number of categories of objects to be identified and counted. The categories of objects may be, for example, the various types of cells making up the blood. The electrical output of the scanner goes to a parameter analyzer 12 and then to a decision matrix 13 which also receives information from the cell data storage 14. The parameter analyzer may compute a number of parameters such as for example the number of peaks from the scanner signal, the area under the signal, and the number of times the signal crosses zero. The cell data storage 14 has informatin stored on these same parameters for each type of cell to be identified. The output of the decision matrix is connected through a cell classifier 15 and a cell counter 16. Cell counter 16 provides a tally by category or type. The output or outputs from the cell counter pass to the correction apparatus 17 and then to a printout-display 18. The system, except for the correeection apparatus 17, is known and is of the nature of the blood cell analyzer described in the article "The LARC Automatic White Blood Cell Analyzer" by Gerhard K. Megla of Corning Glass Co., as published in Acta Cytologica V91. 17, No. 1, January - February 1973, Pages 3–14.

Figure 2:
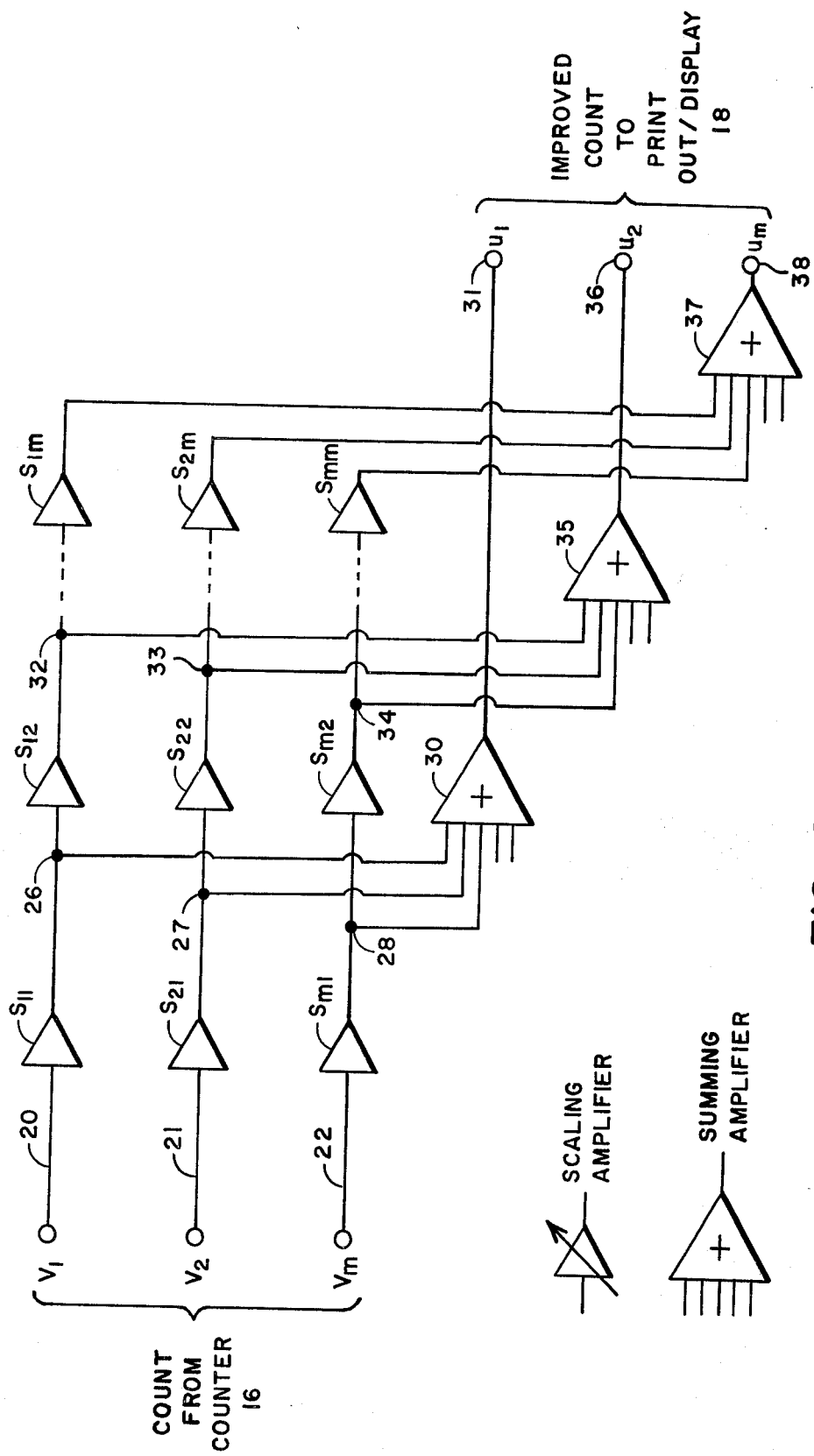

FIG. 2 shows in more detail the correction apparatus 17. Let it be assumed that cell counter 16 provides a separate output count signal on a separate line for each category of object or blood cell and for explanatory purposes let this be limited to three lines $v_1$, $v_2$, and $v_3$ ($m=3$ for this case) which present, respectively, the tally of human blood cells in the categories, Monocytes, Lymphocytes and Neutrophils which have been observed by scanner 10, classified and counted.

It has been found that blood cell analyzer-counter machines have limitations in terms of classification and provide outputs $v_1$, $v_2$, and $v_m$ which have a bias or systematic error in the counted number of cells in each category. Let it be assumed that the actual tally of Monocytes, Lymphocytes and Neutrophils seen by scanner 10 is $n_1$, $n_2$, and $n_m$ and that the tally from the counter is $v_1$, $v_2$, and $v_m$. The numbers $v_1$, $v_2$, and $v_m$ denote the number of cells of each type indicated by the classifier-counter. The numbers $n_1$, $n_2$ and $n_m$ denote the actual number of cells of each type in the sample 11. It has been found that the machine can be analyzed as a stochastic system, and considering the fraction of $n_i$ which contributes to $v_j$, there is a matrix $[r_{ij}]$ of random variables such that $$\begin{pmatrix} v_1 \\ v_2 \\ \vdots \\ v_m \end{pmatrix} = \begin{pmatrix} r_{11} & r_{12} & \cdots & r_{1m} \\ \vdots & & & \vdots \\ r_{m1} & r_{m2} & \cdots & r_{mm} \end{pmatrix} \begin{pmatrix} n_1 \\ n_2 \\ \vdots \\ n_{3n} \end{pmatrix} \quad (1)$$

Let the matrix $[p_{ij}]$ denote the expected value (i.e. average) of $[r_{ij}]$, and let $[p_{ij}]$ be invertible with inverse $[q_{ij}]$. Let the random variables $u_1, u_2, \ldots u_m$, which are the corrected count, be defined by $$\begin{pmatrix} u_1 \\ u_2 \\ \vdots \\ u_m \end{pmatrix} = \begin{pmatrix} q_{11} & q_{12} & \cdots & q_{1m} \\ \vdots & & & \vdots \\ q_{m1} & q_{m2} & \cdots & q_{mm} \end{pmatrix} \begin{pmatrix} v_1 \\ v_2 \\ \vdots \\ v_m \end{pmatrix} \quad (2)$$

Equation (2) is the correction transformation.

Unless $r_{ii} = 1$ for $i = 1, 2, -, m$ it is not usually true that the average values of the random variables $v_i$ in (1) are equal to $n_i$. However, the average values of the random variables $u_i$ in (2 are equal to $n_i$.

FIG. 2 discloses apparatus which implements the correction transformation, that is, equation (2). Input lead 20 carrying machine count $v_i$ is connected through scaling amplifier or constant multiplier $s_{11}$, lead 21 carrying count $v_2$ is connected through scaling amplifier $s_{21}$, and lead 22 carrying count $v_m$ is connected through scaling amplifier $s_{m1}$ to terminals 26, 27 and 28 respectively. The scaling amplifiers may be, for example, resistive networks or amplifiers, as required, and may have a gain of less than, equal to, or greater than 1, and the sign may be positive or negative, as required. These terminals 26, 27 and 28 are connected to the inputs of a summing amplifier 30 the output of which is brought out at a terminal 31. Scaling amplifier $s_{11}$ scales according to a value $q_{11}$, $s_{21}$ to a value $q_{21}$ and $s_{m1}$ to a value $q_{m1}$ according to the matrix of Equation 2.

above example. The following small sample counting and correction example is typical

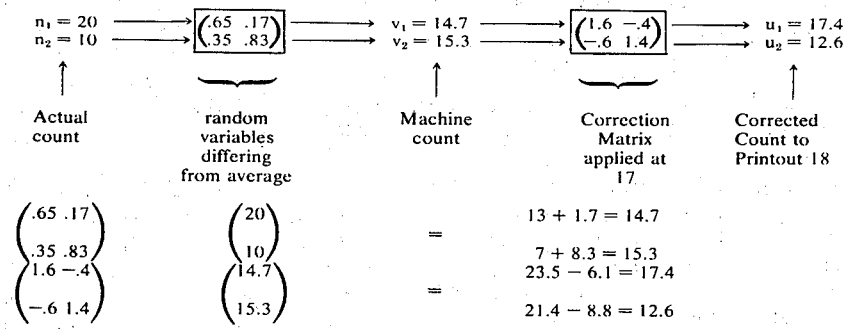

Actual count — random variables differing from average — Machine count — Correction Matrix applied at 17 — Corrected Count to Printout 18

$$\begin{pmatrix} .65 & .17 \\ .35 & .83 \end{pmatrix} \begin{pmatrix} 20 \\ 10 \end{pmatrix} = \begin{matrix} 13 + 1.7 = 14.7 \\ 7 + 8.3 = 15.3 \end{matrix}$$

$$\begin{pmatrix} 1.6 & -.4 \\ -.6 & 1.4 \end{pmatrix} \begin{pmatrix} 14.7 \\ 15.3 \end{pmatrix} = \begin{matrix} 23.5 - 6.1 = 17.4 \\ 21.4 - 8.8 = 12.6 \end{matrix}$$

Terminals 26, 27 and 28 described above are also connected, respectively, to the inputs of scaling amplifiers $s_{12}$, $s_{22}$ and $s_{m2}$, the output terminals of which are numbered 32, 33 and 34. Terminals 32, 33 and 34 are connected to the inputs of a summing amplifier 35 the output of which is brought out at a terminal 36. Terminals 32, 33 and 34 are further connected, respectively, to the inputs of scaling amplifiers $s_{1m}$, $s_{2m}$ and $s_{mm}$ and the outputs of these scaling amplifiers are fed to a summing amplifier 37, the output of which is brought out at a terminal 38. Scaling amplifiers $s_{12}$, $s_{22}$ and $s_{m2}$ provide, at their outputs, the signal values of $v_1 q_{12}$, $v_2 q_{22}$ and $v_m q_{m2}$ and scaling amplifiers $s_{1m}$, $s_{2m}$ and $s_{mm}$ provide at their outputs the signal values of $v_1 q_{1m}$, $v_2 q_{2m}$ and $v_m q_{mm}$, respectively, to satisfy the matrix of Equation 2. The number of scaling amplifiers is thus at least equal to the number of non zero elements of the correction matrix, the number of elements being equal to the square of the number of types of objects being counted. The scaling amplifiers may each have gain controls to allow the individual adjustment of the gain from zero to more than unity (positive or negative) in each scaling amplifier. While amplifiers $s_{11}$, $s_{12}$ and $s_{1m}$ have been shown as being connected in series, they may equally as well have their inputs be connected in parallel to line 20. Then the inputs of $s_{21}$, $s_{22}$ and $s_{2m}$ would also be in parallel to line 21 and likewise the inputs of $s_{m1}$, $s_{m2}$ and $s_{mm}$ to line 22. Thus it may be understood that the correction apparatus of FIG. 2 accepts at its input the counts from the counter 16 (i.e. biased estimates of numbers of Monocytes ($v_1$), Lymphocytes ($v_2$), and Neutrophils ($v_3$)) and provides to the printout 18, at output terminals 31, 36 and 38, the improved or corrected counts $u_1$, $u_2$ and $u_m$.

As a simplified numerical example, assume the classifier counter recognizes two categories. It is given known cells of category $n_1$ of which, on the average, it correctly recognizes 70% and misrecognizes 30% as category $n_2$. Further assume the machine is given known cells of category $n_2$ of which on the average it correctly recognizes 80% and misrecognizes 20% as category $n_1$. Thus the correction matrix of equation (2) is given by $$\begin{pmatrix} q_{11} & q_{12} \\ q_{21} & q_{22} \end{pmatrix} = \begin{pmatrix} 1.6 & -.4 \\ -.6 & 1.4 \end{pmatrix}$$

As is often the case the machine is working with small samples so that the averages of the random variables in the classifying are deviate from the averages of the above example.

In the immediate above small sample example it may be appreciated that the random variable averages estimated by sampling have strayed considerably from the random variable averages and for that reason the correction apparatus, based on the large sample average bias is effective to significantly improve the correctness of the count but does not completely erase the errors in all cases.

The embodiments of the invention in which an exclusive property or right is claimed are defined as follows:

1. In a count correction apparatus for a system classifies classified objects by type to provide a signal readout of the count of the objects of each type, and further in which system there is a bias or error in the count of objects of each type because of limitations in the classifying, the average systematic errors being expressible by the matrix relation $$\begin{pmatrix} v_1 \\ v_2 \\ \vdots \\ v_m \end{pmatrix} = \begin{pmatrix} p_{11} & p_{12} & \cdots & p_{1m} \\ & - & - & - & - \\ p_{m1} & p_{m2} & \cdots & p_{mm} \end{pmatrix} \begin{pmatrix} n_1 \\ n_2 \\ \vdots \\ n_m \end{pmatrix} \quad (1)$$

and being correctible according to the inverse matrix relation $$\begin{pmatrix} u_1 \\ u_2 \\ \vdots \\ u_m \end{pmatrix} = \begin{pmatrix} q_{11} & q_{12} & \cdots & q_{1m} \\ & - & - & - & - \\ q_{m1} & q_{m2} & \cdots & q_{mm} \end{pmatrix} \begin{pmatrix} v_1 \\ v_2 \\ \vdots \\ v_m \end{pmatrix} \quad (2)$$

where the matrix with elements $q_{ij}$ is the inverse of the matrix with elements $p_{ij}$, where $n_1, n_2, n_m$ is the actual number of objects of each type, $v_1, v_2, v_m$ is the machine count, and $u_1, u_2, u_m$ is the improved count, the improvement comprising:

count correction means connected to receive the signal count of objects by type comprising a network of scaling amplifiers and summing amplifiers, the number of summing amplifiers being equal to the number ($m$) of types of objects being counted, the number of matrix elements in the correction matrix being equal to the square of the number of types of objects being counted, and the number of scaling amplifiers $S_{11}$, $S_{12}$, ——, $S_{1m}$; $S_{21}$, $S_{22}$, ——, $S_{2m}$; ——; $S_{m1}$, $S_{m2}$, ——, $S_{mm}$ being at least equal to the number of non-zero elements of the correction matrix, said scaling amplifiers $S_{11}$, $S_{12}$, ——, $S_{1m}$ each connected to receive a signal the magnitude of which is a function of the count of one of said types, said scaling amplifiers $S_{21}, S_{22}, —, S_{2m}$ each connected to receive a signal the magnitude of which is a function of the count of a second of said types, the remaining scaling amplifiers being connected in like manner to receive the count of other types, each of said scaling amplifiers corresponding in gain and sign to a different element of said correction matrix, the outputs of said scaling amplifiers $S_{11}, S_{21}, ——, S_{m1}$ being connected to sum at one of said summing amplifiers, the outputs of said scaling amplifiers $S_{12}, S_{22}, —, S_{m2}$ being connected to sum at the second summing amplifier, the remaining scaling amplifiers being connected in like manner to other summing amplifiers, whereby the outputs of said summing amplifiers provide, respectively, an improved accuracy count signal of each type of object.

2. The invention of claim 1 in which the system is a blood cell classifier-counter and in which the objects to be classified are blood cell types such as Monocytes, Lymphocytes and Neutrophils.

3. The invention of claim 1 in which the scaling amplifiers are individually controllable in sign and in gain from approximately zero to in excess of unity gain.

4. A blood cell classifier-counter apparatus which classifies individual blood cells into types and provides a count of the number of cells of each type, comprising in combination:
  means for scanning a blood sample and for providing output signals characteristic of the various cell types of the blood as the cells are scanned;
  classifying means for receiving said output signals and classifying said signals into blood cell types;
  counting means connected to said classifying means and providing a count of the number of cells of each blood cell type, said classifying means and counting means being subject to a number of random errors which, on the average, tend to appear as a systematic bias or error in the classification and count of cells of each type, thereby providing a biased count, said biased count having errors expressible by the matrix relation $$\begin{pmatrix} v_1 \\ v_2 \\ \vdots \\ v_m \end{pmatrix} = \begin{pmatrix} r_{11} & r_{12} & \cdots & r_{1m} \\ & - & - & - & - \\ r_{m1} & r_{m2} & \cdots & r_{mm} \end{pmatrix} \begin{pmatrix} n_1 \\ n_2 \\ \vdots \\ n_m \end{pmatrix}. \quad (1)$$

and count correction means connected to said counting means to receive said biased counts wherein count correction is expressible by the correction inverse matrix relation $$\begin{pmatrix} u_1 \\ u_2 \\ \vdots \\ u_m \end{pmatrix} = \begin{pmatrix} q_{11} & q_{12} & \cdots & q_{1m} \\ & - & - & - & - \\ q_{m1} & q_{m2} & \cdots & q_{mm} \end{pmatrix} \begin{pmatrix} v_1 \\ v_2 \\ \vdots \\ v_m \end{pmatrix}. \quad (2)$$

said count correction means having a corrective effect on said systematic bias to provide an output count of improved accuracy to count utilizing means, where
  $n_1, n_2, n_m$ is the actual number of objects of each type,
  $v_1, v_2, v_m$ is the machine count,
  $u_1, u_2, u_m$ is the improved count,
the matrix with elements $q_{ij}$ is the average value of the matrix with elements $r_{ij}$; said count correction means comprising a network of scaling amplifiers and summing amplifiers, the number of summing amplifiers being equal to the number ($m$) of types of objects being counted, the number of matrix elements in the correction matrix being equal to the square of the number of types of objects being counted, and the number of scaling amplifiers $S_{11}, S_{12}, —, S_{1m}; S_{21}, S_{22}, —, S_{2m}; —; S_{m1}, S_{m2}, —, S_{mm}$ being at least equal to the number of non-zero elements of the correction matrix, said scaling amplifiers $S_{11}, S_{12}, —, S_{1m}$ each connected to receive a signal the magnitude of which is a function of the count of one of said types, said scaling amplifiers $S_{21}, S_{22}, —, S_{2m}$ each connected to receive a signal the magnitude of which is a function of the count of a second of said types, the remaining scaling amplifiers being connected in like manner to receive the count of other types, each of said scaling amplifiers corresponding in gain and sign to a different element of said correction matrix, the outputs of said scaling amplifiers $S_{11}, S_{21}, —, S_{m1}$ being connected to sum at one of said summing amplifiers, the outputs of said scaling amplifiers $S_{12}, S_{22}, —, S_{m2}$ being connected to sum at the second summing amplifier, the reamining scaling amplifiers being connected in like manner to other summing amplifiers, whereby the outputs of said summing amplifiers provide, respectively, an improved accuracy count signal of each type of object.

* * * * *